US00PP19928P2

(12) United States Plant Patent
Trees

(10) Patent No.: US PP19,928 P2
(45) Date of Patent: Apr. 14, 2009

(54) ***LANTANA* PLANT NAMED 'BALANDLAE'**

(50) Latin Name: *Lantana camara*
Varietal Denomination: Balandlae

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/895,180

(22) Filed: Aug. 23, 2007

(51) Int. Cl.
*A01H 5/00* (2006.01)

(52) U.S. Cl. ..... Plt./227
(58) Field of Classification Search ..... Plt./227
See application file for complete search history.

(56) References Cited

U.S. PATENT DOCUMENTS

2008/0184417 P1 * 7/2008 Pan ..... Plt./227

* cited by examiner

*Primary Examiner*—Wendy C. Haas
(74) *Attorney, Agent, or Firm*—Audrey Charles

(57) ABSTRACT

A new and distinct cultivar of *Lantana* plant named 'Balandlae', characterized by its reddish-pink and yellow-orange inflorescences, dark green-colored foliage, and moderately vigorous, mounded, and spreading growth habit.

1 Drawing Sheet

Latin name of genus and species of plant claimed: *Lantana camara.*
Variety denomination: 'Balandlae'.

BACKGROUND OF THE INVENTION

The present invention relates to a new and distinct cultivar of *Lantana* plant botanically known as *Lantana camara* and hereinafter referred to by the cultivar name 'Balandlae'.

The new cultivar originated in a controlled breeding program in Arroyo Grande, Calif. during July 2003. The objective of the breeding program was the development of *Lantana* cultivars with continuous flowering, dark green-colored foliage, and a well-branched, vigorous growth habit.

The new *Lantana* cultivar was the result of a self-pollination of the proprietary *Lantana camara* breeding selection designated BFP 958-A, not patented, characterized by its pink and yellow bicolored inflorescences, dark green-colored foliage, and upright-mounded growth habit. The new cultivar was discovered and selected as a single flowering plant within the progeny of the above stated self-pollination during April 2004 in a controlled environment at Arroyo Grande, Calif.

Asexual reproduction of the new cultivar by terminal stem cuttings since April 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balandlae' as a new and distinct cultivar of *Lantana* plant:

1. Reddish-pink and yellow-orange bicolored inflorescences;
2. Dark green-colored foliage; and
3. Moderately vigorous, mounded, and spreading growth habit.

Plants of the new cultivar differ from plants of the parent primarily in growth habit.

Of the many commercially available *Lantana* cultivars known to the inventor, the most similar in comparison to the new cultivar is Bandana Red 'Bante Reeda', U.S. Plant Patent Application Publication Number 20080184417, now abandoned. However, in side by side comparisons, plants of the new cultivar differ from plants of 'Bante Reeda' in the following characteristics:

1. Plants of the new cultivar have more inflorescences than plants of 'Bante Reeda';
2. Plants of the new cultivar are larger, as measured by height and width, than plants of 'Bante Reeda'; and
3. Plants of the new cultivar have a flower color different from plants of 'Bante Reeda'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balandlae'. The plants were grown in 4.5 inch pots for 7 weeks in a greenhouse at West Chicago, Ill. Plants were given one pinch at transplant.

DETAILED BOTANICAL DESCRIPTION

Figure 1:
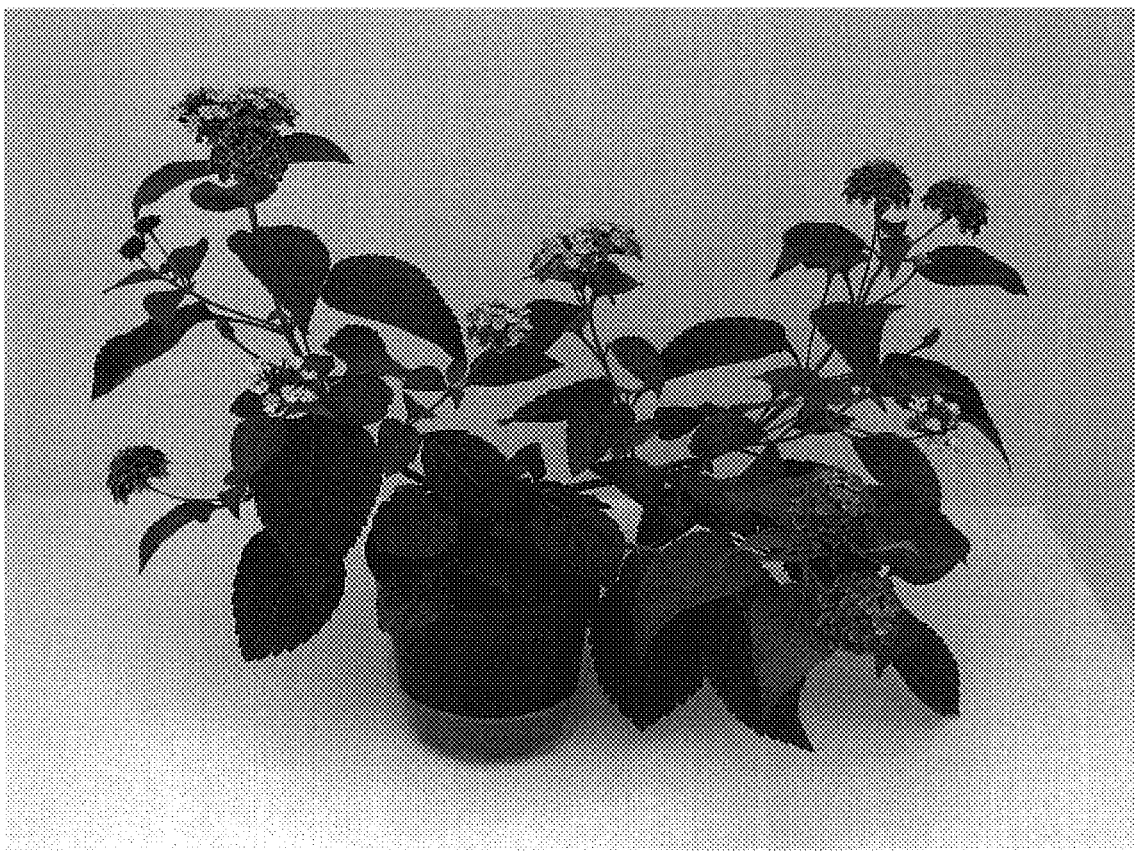
FIG. 1 illustrates a side view of the overall growth and flowering habit of 'Balandlae'.
Figure 2:
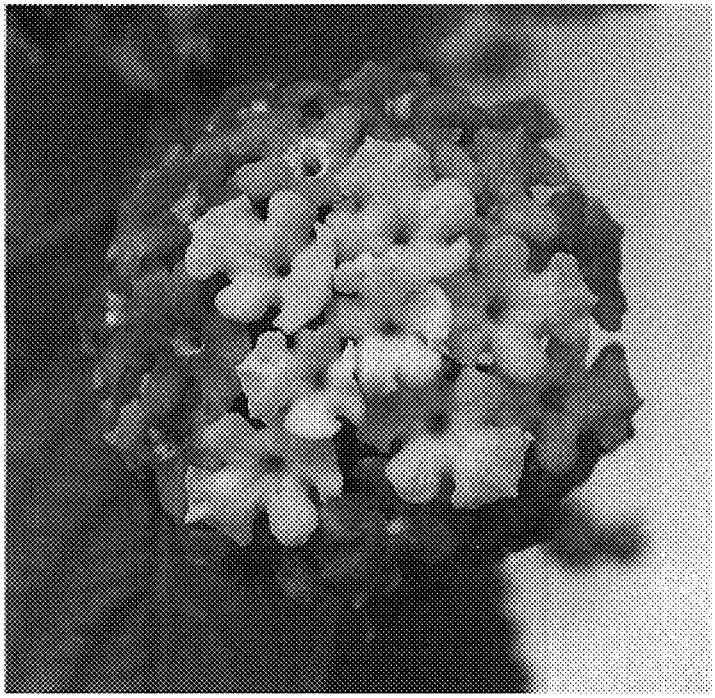
FIG. 2 illustrates a close-up view of an individual inflorescence of 'Balandlae'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 9, 2007 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 7 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Lantana camara* cultivar 'Balandlae'.

Parentage:

*Parent.*—Proprietary *Lantana camara* breeding selection designated BFP 958-A, not patented.

Propagation:

*Type cutting.*—Terminal stem.

*Time to initiate roots.*—Approximately 7 to 11 days.

*Time to produce a rooted cutting.*—Approximately 24 to 28 days.

*Root description.*—Fibrous.

*Rooting habit.*—Freely branching.

Plant description:

*Commercial crop time.*—Approximately 7 to 8 weeks from a rooted cutting to finish in a 15 cm pot.

*Growth habit and general appearance.*—Moderately vigorous, mounded, and spreading.

*Size.*—Height from soil level to top of plant plane: Approximately 24.2 cm. Width: Approximately 37.4 cm.

*Branching habit.*—Freely branching, pinching enhances branching. Quantity of lateral branches per plant: Approximately 6.

*Branch.*—Shape: Square in cross section. Strength: Strong, becomes woody with age. Length: Approximately 16.2 cm. Diameter: Approximately 3.0 mm. Length of central internode: Approximately 4.6 cm. Texture: Densely pubescent with a mixture of glandular and nonglandular hairs. Gland color: Colorless, transparent. Color of young stem: 144A. Color of mature stem: 199B.

Foliage description:

*General description.*—Quantity of leaves per lateral branch: Approximately 6. Fragrance: Strong, spicy. Form: Simple. Arrangement: Opposite.

*Leaves.*—Aspect: Perpendicular to obtuse angle to stem. Shape: Ovate. Margin: Serrate. Apex: Acute. Base: Obtuse. Venation pattern: Pinnate. Length of mature leaf: Approximately 8.9 cm. Width of mature leaf: Approximately 5.8 cm. Texture of upper surface: Scabrous. Texture of lower surface: Scabrous with a mixture of glandular pubescence along venation. Gland color: Colorless, transparent. Color of upper surface of young foliage: 137A with venation of 137B. Color of lower surface of young foliage: 137C with venation of 138C. Color of upper surface of mature foliage: Closest to 139A with venation of 137B. Color of lower surface of mature foliage: 137B with venation of 138C.

*Petiole.*—Length: Approximately 2.4 cm. Diameter: Approximately 2.0 mm. Texture: Scabrous with a mixture of glandular pubescence. Gland color: Colorless, transparent. Color: 144A.

Flowering description:

*Flowering habit.*—'Balandlae' is freely flowering under outdoor growing conditions with substantially continuous blooming from spring through autumn and year-round in greenhouse environment.

*Lastingness of individual inflorescence on the plant.*—Approximately 10 to 12 days from first color of outer buds to dropping of last flower.

Inflorescence description:

*General description.*—Type: Corymb. Quantity per plant: Approximately 14. Fragrance: Strong, spicy. Aspect: Facing upward or outward. Height: Approximately 2.4 cm. Width: Approximately 3.5 cm. Quantity of fully open flowers per inflorescence: Approximately 38.

*Peduncle.*—Strength: Strong. Shape: Square in cross section. Aspect: Acute angle to stem. Length: Approximately 2.7 cm. Diameter: Approximately 1.0 mm. Texture: Scabrous and glandular pubescent. Gland color: Colorless, transparent. Color: 144A.

Flower description:

*General description.*—Type: Salverform.

*Bud.*—Rate of opening: Generally takes 1 to 2 days for bud to progress from first color to fully open flower. Buds open in progression from the margin to the center of the inflorescence. Quantity of unopened inflorescences per plant: Approximately 6.

*Bud just before opening.*—Shape: Elongated, rectangular at apex. Length: Approximately 7.5 mm. Diameter: Approximately 2.0 mm. Color: 29A.

*Corolla.*—Depth: Approximately 1.6 cm. Diameter: Approximately 1.1 cm.

*Petals.*—Quantity: 4, non-imbricate, non-symmetrical. Petals are fused at base forming a corolla tube. Shape: Obovate. Appearance: Dull. Aspect: Flat. Margin: Entire, ruffled. Apex: Obtuse. Length of upper petal from throat: Approximately 4.8 mm. Width of upper petal: Approximately 7.0 mm. Length of lateral petals from throat: Approximately 4.0 mm. Width of lateral petals: Approximately 4.0 mm. Length of lower petal from throat: Approximately 5.0 mm. Width of lower petal: Approximately 7.0 mm. Texture of upper surface: Glabrous. Texture of lower surface: Densely pubescent with a mixture of glandular and nonglandular hairs. Pubescence is a mixture of colorless and 53B. Color of upper surface when first open: 13B with 29B at margin. Color of lower surface when first open: 13B with an overlay of 34B on lateral petals. Color of upper surface when fully open: 26B with an overlay of 53B, transitioning with age to N74B with an overlay of N74A in center of flower. Prior to senescence, petal color transitions to 53A. Color of lower surface when fully open: 53D transitioning with age to N74D.

*Corolla tube.*—Length: Approximately 1.1 cm. Diameter at tube opening: Approximately 1.0 mm. Diameter at base: Approximately 1.0 mm. Texture of inner surface: Densely pubescent. Texture of outer surface: Glabrous at base, gradually becoming densely pubescent at tube opening with a mixture of glandular and nonglandular hairs. Pubescence is a mixture of colorless and 53B. Color of inner surface: 145D. Color of outer surface: 145C at base, transitioning at midpoint to 145D with an overlay of 53D.

*Calyx.*—Shape: Tubular with two broadly acute tips. Length: Approximately 2.0 mm. Diameter at tip: Approximately 1.0 mm. Diameter at base: Approximately 1.0 mm. Texture of inner surface: Glabrous. Texture of outer surface: Densely pubescent with a mixture of glandular and nonglandular hairs. Gland color: Colorless, transparent. Color of inner and outer surfaces: 144D.

*Bracts.*—Quantity per flower: 1 per flower. Shape: Lanceolate. Length: Approximately 4.0 mm. Width: Approximately 1.0 mm. Texture of upper surface: Sparsely pubescent with a mixture of glandular and nonglandular hairs. Gland color: Colorless, transparent. Texture of lower surface: Densely pubescent with a mixture of glandular and nonglandular hairs. Gland color: Colorless, transparent. Color of upper and lower surfaces: 144B.

*Reproductive organs.*—Androecium: Stamen quantity: 4 per flower, adnate to corolla tube. Stamen length: Approximately 2.0 mm. Anther shape: Ovoid, bilobed. Anther length: Less then 1 mm. Anther color: 12B. Pollen amount: Sparse. Pollen color: 12C. Gynoecium: Pistil quantity: 1 per flower. Pistil length: Approximately 4.0 mm. Stigma shape: Funnel. Stigma length: Less than 1 mm. Stigma color: 144B, translucent. Style length: Approximately 3.0 mm. Style color: 145D. Ovary diameter: Approximately 1.0 mm. Ovary color: N144C.

Seed and fruit production: Neither seed nor fruit production has been observed.

Disease and pest resistance: Resistance to pathogens and pests common to *Lantana* has not been observed.

What is claimed is:

1. A new and distinct cultivar of *Lantana* plant named 'Balandlae', substantially as herein shown and described.

* * * * *